United States Patent
Feries

(10) Patent No.: US 6,479,081 B2
(45) Date of Patent: *Nov. 12, 2002

(54) METHOD FOR OBTAINING GRAPE TANNIN, RESULTING TANNIN AND USES

(75) Inventor: Marc Feries, Saint-Montan (FR)

(73) Assignee: Ferco, Saint-Montan (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/582,699

(22) PCT Filed: Dec. 30, 1998

(86) PCT No.: PCT/FR98/02923

§ 371 (c)(1),
(2), (4) Date: Sep. 20, 2000

(87) PCT Pub. No.: WO99/35239

PCT Pub. Date: Jul. 15, 1999

(65) Prior Publication Data

US 2002/0028259 A1 Mar. 7, 2002

(30) Foreign Application Priority Data

Dec. 30, 1997 (FR) .............................. 97 16860

(51) Int. Cl.⁷ .............................................. A61K 35/78
(52) U.S. Cl. ........................ 424/766; 424/776; 424/777
(58) Field of Search ................................ 424/766, 776, 424/777

(56) References Cited

U.S. PATENT DOCUMENTS

| | | | | |
|---|---|---|---|---|
| 4,211,577 A | * | 7/1980 | Wallin | |
| 4,260,388 A | * | 4/1981 | Mirabel et al. | |
| 4,481,226 A | * | 11/1984 | Crosby et al. | |
| 4,500,556 A | * | 2/1985 | Langston | |
| 4,735,807 A | * | 4/1988 | Thyfault | |
| 5,141,611 A | * | 8/1992 | Ford | |
| 5,904,924 A | * | 5/1999 | Gaynor et al. | |
| 5,912,363 A | | 6/1999 | Nafisi-Movaghar et al. | |
| 6,099,854 A | * | 8/2000 | Howard et al. | |

FOREIGN PATENT DOCUMENTS

| FR | A-2 372 823 | 6/1978 |
|---|---|---|
| FR | A1-2 643 073 | 8/1990 |

OTHER PUBLICATIONS

Oszmianski et al. J. Agric. Food Chem. vol. 37, No. 5, pp. 1293–1297, abstract enclosed, 1989.*
USANA Technical Bulletin titled "Grape Seed Extract", 4 pages, from website usana.com, Oct. 1997.*
Oszmianski et al. Am. J. Enol. Vitic. vol. 37, No. 1, pp. 7–12, 1986.*
Tamborra et al. Riv. Vitic. Enol. vol. 48, No. 4, pp. 39–52, abstract enclosed, 1995.*
B. Mandzhukov et al., Effect of some factors on the extraction of phenolic compounds from grapes, 6001 Chemical Abstracts, vol. 88, No. 11, pp. 380, 1977.

* cited by examiner

Primary Examiner—Christopher R. Tate
(74) Attorney, Agent, or Firm—Oliff & Berridge, PLC

(57) ABSTRACT

The invention concerns a method for obtaining grape pomace and/or seed tannin, comprising steps which consist in: (a) from fresh black or white grapes pomace and/or seed, carrying out a solid-liquid extraction of raw tannin fraction in an aqueous solvent; (b) eliminating the first solvent from the resulting extract to obtain a concentrate of the raw tannin fraction; and (c) purifying the raw tannin fraction to obtain said tannin: The method is characterised in that in step (a) sulphite water ($H_2O+SO_2$) is used as solvent, and in step (c) the raw tannin fraction is purified by selectively adsorbing the tannin polyphenol compounds on resin and by subsequent filtering. The invention also concerns the resulting tannin and its uses in particular as endogenous tannin in wine.

9 Claims, No Drawings

METHOD FOR OBTAINING GRAPE TANNIN, RESULTING TANNIN AND USES

The present invention relates to the production, from fresh black or white grapes, of grape tannin from the marc or seed, containing a high content of polyphenolic compounds, the tannin thus obtained and the uses thereof especially in oenology.

Tannins are substances of plant origin which consist of polyphenolic compounds and which are divided into two main groups, catechuic tannins also called condensed or procyanidin tannins, to which the grape tannins belong, and the hydrolysable tannins predominantly comprising gallotannins and ellagitannins. Grape tannins are naturally present in grape skins and seeds.

These two groups are distinguishable by the nature of the polyphenolic compounds which they contain. The catechuic tannins resemble catechuic derivatives and procyanidolic oligomers and polymers consisting of 3-flavanol and 3,4-flavanediol units. More particularly, grape seed and skin tannins consist of catechin, epicatechin and epicatechin-3-O-gallate, the skin tannin containing, in addition, epigallocatechin which is absent from seed tannin. The polymers of skin tannin are longer (chains of up to 80 units) than the polymers of seed tannin (chains not exceeding 30 to 35 units). Finally, there are grafted on seed tannin molecules of gallic acid which is only present in very small quantities in skin tannin.

Gallotannins of the hydrolysable tannin group consist of polymers of glucose and of gallic acid and the ellagitannins of the same group consist of a polymer of glucose and of ellagic, gallic and/or hexahydroxydiphenic acids.

In oenology, tannins are used for the clarification of wines because they exhibit a strong affinity to bind to proteins. They are also used for improving the organoleptic qualities and the taste characters of wines.

Tannins extracted from chestnut tree, oak tree and nut galls of various trees, which are hydrolysable tannins, are mainly used.

The application of tannins is not limited to oenology, but it extends to many other sectors such as the tanning, agri-food, pharmaceutical, cosmetic, ceramic and textile sectors and the like.

Grape tannins are not used on an industrial scale in the manufacture of wines because of the low content of phenolic compounds in the extracts obtained. Indeed, the methods currently used for preparing grape tannins cause substantial degradation of the said compounds.

Despite the small proportion of polyphenolic compounds which they contain, grape tannins, and more particularly grape seed tannins, are used in the pharmaceutical sector as a medicament in particular for treating venous insufficiency-related disorders. The active ingredient is the fraction of procyanidolic oligomers contained in the tannin. However, because of the high degradability of these tannins, the purity, in relation to the said oligomers, of the medicaments currently available does not exceed 20%.

The method of production which is conventionally followed for obtaining tannins, grape tannins for example, consists in: (a) carrying out, starting with fresh black and/or white grape marc and/or seed, a solid-liquid extraction of a crude tannin fraction in an aqueous solvent, (b) removing the aqueous solvent from the resulting extract in order to obtain a concentrate of the crude tannin fraction, and (c) purifying the crude tannin fraction in order to obtain the said tannin, by a liquid-liquid extraction, evaporation of the solvent in which the tannin in solubilized and then filtration on activated charcoal.

According to the present invention, there is provided a method for producing a tannin having a high content of polyphenolic compounds, the said method incorporating defined stages such that they make it possible to preserve the integrity of the said compounds.

The method of the invention is characterized in that, in combination, according to stage (a) sulphited water ($H_2O + SO_2$) is used as solvent, and according to stage (c) the crude tannin fraction is purified by selective adsorption of the polyphenolic compounds of the tannin on resin and subsequent filtration.

Before disclosing the present invention in greater detail, various terms used in the description and the claims are defined below.

The grape marc comprises the grape stalk, that is to say the bunch without its grapes (peduncle and pedicels) and the skin which constitutes the envelope of the grape berry.

Grape marc tannin is therefore understood to mean the tannin obtained by treating the grape marc as defined above. However, given that the substances constituting the marc tannin are in fact obtained mainly from the grape skin, this expression ought to more precisely be understood to mean a grape skin tannin. In oenology, the marc is in fact a portion of the grapes harvested for winemaking, of white wine only, which is recovered after pressing the grape juice and then separating out the seeds. Accordingly, it generically designates the skin. Thus, according to the method of the invention, when the starting material is fresh grape marc, it will be understood that this may be the skin of fresh grape alone.

Fresh grape is understood to mean according to the invention a grape which has not been subjected to alcoholic fermentation or acetic fermentation.

The nature of the total phenolic compounds varies according to the type of tannin, as specified above. Their content is however always determined as equivalent gallic acid, according to the tannic acid technique of the international oenological codex.

Using the method of the invention, a tannin is obtained which comprises in particular gambiriines which are dimers. The tannin from the skin and the stalk according to the method described above comprises, in addition, resveratrol. The tannin from the skin also comprises various flavonols such as quercetin and kaempferol.

Advantageously, the method is defined by the following additional characteristics, taken in combination or otherwise:

stage (a) is carried out at a temperature at most equal to 25° C., and preferably of between 15 and 25° C., stage (b) is carried out by evaporation under vacuum at a temperature at most equal to 75° C., after evaporation according to stage (b), the concentrate of the crude tannin fraction is immediately cooled to a temperature at most equal to 30° C., the method comprises a stage (b'), between stages (b) and (c), according to which a fermentation of the concentrate of the crude tannin fraction is carried out; for the purposes of stage (b'), yeasts in suspension in a liquid medium are inoculated into the concentrate of the crude tannin fraction; the fermentation is allowed to proceed; the alcohol formed is removed followed by the particles in suspension in order to obtain a concentrate of the fermented crude tannin fraction.

The objective of the fermentation is the conversion of sugars to alcohol as well as the beneficial conversion of the tannins. This conversion makes the tannins conform to the organoleptic requirements of wines, because they undergo the same process of conversion as the intrinsic tannins of the wine.

according to stage (c), the crude tannin fraction is adsorbed on a resin, of the preferably microcrosslinked styrene divinylbenzene (DVB) type, according to stage (c), the crude tannin fraction treated on resin is filtered by diafiltration, in particular selective diafiltration; the latter is advantageously carried out at a temperature at most equal to 25° C.

Other subjects of the invention are:

the black and/or white grape marc tannin which can be obtained by the method of the invention, comprising a content of total polyphenolic compounds of at least about 300 mg equivalent gallic acid per g of dry matter, and the black and/or white grape seed tannin which can be obtained by the method of the invention, comprising a content of total polyphenolic compounds of at least about 500 mg equivalent gallic acid per g of dry matter.

The invention relates, in addition, to the use of a white grape marc tannin as defined above, as endogenous tannin in wine. It also relates to the use of a grape tannin of the invention for producing an extract rich in procyanidolic oligomers.

The present invention is now illustrated with the aid of the following example.

EXAMPLE

1) Raw Material

According to this illustration of the method of the invention, fresh, white grape marc is chosen which is pressed the same day. It is possible to use whole marc (stalks, skins and seeds) or alternatively destemmed marc (skins and seeds), pressed to a greater or lesser degree but not dilacerated.

The juice or must which impregnates the marc should not have undergone alcoholic fermentation or acetic fermentation.

Advantageously the skin is yellow to greenish yellow and should in particular have no brown colour, the sign of oxidations and degradations, and the stalk, if present, is clearly green.

2) Stage (a) of Solid-liquid Extraction

First Solvent

Demineralized water, sulphited with 1 to 1.5 g of sulphur dioxide per litre.

Materials and Principles of Extraction

A diffusion battery is used which is composed of 5 to 10 extraction stages and is described below.

It constitutes an alignment of tanks made of concrete, having the shape of a parallelepiped rectangle which may contain from 10 to 50 tons of marc.

A pumping system aspirates the liquid at the bottom of the tank and discharges it at the surface of the marc, which makes it possible to carry out a complete, but nonviolent, gradual washing.

The resulting extract then circulates from one tank to another so as to become enriched with polyphenolic compounds.

Extraction Parameters

Duration

It varies from 2 to 6 hours per washing cycle for the same cuve, before the extract is moved to the next cuve to pursue the polyphenolic compounds enrichment.

This duration is determined according to the richness in polyphenolic compounds and the structure of the starting marc.

Temperature

It varies from 15 to 25° C.

A rise would be damaging to the quality of the tannin obtained, and would bring about the extraction of other undesirable compounds.

Furthermore, an excessively high temperature would promote losses of $SO_2$ as well as a risk of fermentation of the sugars present into alcohol. This formation of alcohol is particularly disadvantageous because the slightest trace of alcohol will cause the extraction of polyphenolic compounds which are undesirable and furthermore very difficult to subsequently remove;

3) Stage (b) of Removal of the First Solvent

Materials

The equipment intended for the triple effect concentration under vacuum is made of stainless steel 316, and is provided with a sulphite remover.

A condenser having a sufficient surface area to rapidly reach a temperature of less than 30° C. is placed at the outlet.

Principle

The extract obtained in 2) [stage (a)] should be brought to a dry matter content (including the fermentable sugars) which corresponds to a density of 1.080 to 1.100 at 20° C., by removing the water and the $SO_2$, by evaporation under vacuum at a maximum temperature of 75° C.

The concentrate of the crude tannin fraction obtained is immediately cooled to between 26 and 28° C., for the next fermentation stage (b').

4) Stage (b') of Fermentation

Inoculation and Fermentation

The concentrate obtained in b) [stage (b)] is inoculated with oenological yeasts and fermentation activators.

The temperature during fermentation preferably does not exceed 25° C.

As soon as the fermentation ends, the fermented crude tannin fraction is cooled to 15° C. This cooling makes it possible to obtain sufficient clarification by settling for the removal of the alcohol formed (or dealcoholization).

Removal of the Alcohol Formed

For this stage, it is possible to use the same materials as those described in 3).

The operating parameters are essentially the same, with the exception of the supplying rate which will be less, so as not to saturate the concentrator with the alcohol vapours, and therefore to properly recover it.

The principle is identical to that presented in 3), except for the control of the dry matter which, for this stage, is monitored by the refractive index which will be between 12 and 15 Brix.

The cooling temperature at the concentrator outlet is preferably between 10 and 13° C.

The product is maintained stirring, the time necessary for the formation of the crystals of potassium tartrate, which will then precipitate simply by settling and can thus be recovered.

Removal of the Particles in Suspension

The particles in suspension which essentially consist of yeasts, crystals of tartrate, and flocculates of polysaccharides, are removed either by centrifugation or by microfiltration.

5) Stage (c) of Purification

The two techniques described below are used consecutively.

5.1) Purification by Selective Adsorption of the Polyphenolic Compounds in the Tannin Materials Resin columns made of ebonite steel, coated with adsorbent resin of the Styrene DVB type, such as Amberlite XAD 16 MP marketed by Rohm and Haas, are used.

Principle

The treatment of the concentrate of the crude fermented tannin fraction obtained in 4), with the materials described above, comprises two stages:

- a phase of selective attachment of the polyphenolic compounds by adsorption onto the resin, and therefore removal of the compounds other than the polyphenolic compounds, and then
- a phase of elution of the phenolic compounds adsorbed by an ethanol solution at 50° GL.

5.2) Purification, by Membrane Separation, of the Polyphenolic Compounds

Materials

A nanofiltration module equipped with organic membranes having a cut-off of 100 to 300 daltons is used.

Principle

The eluate (polyphenolic compounds in ethanol) obtained in 5.1) is dealcoholized and concentrated by retention of the polyphenolic compounds on the membrane.

It is preferable to use the diafiltration technique because it makes it possible to maximize the dealcoholization.

The operating parameters will then be from 8 to 10 bars at 20° C. maximum.

The resulting permeate (water, ethanol and a few salts) can be recycled for the elution of 5.1) by conventional distillation.

After purification, the eluate concentrated above (or retentate) which has a dry matter content of 10 to 15%, is then dried, by conventional spray-drying with the following parameters:

tower inlet air temperature: 190° C.

tower outlet air temperature: 85° C.

This method makes it possible to obtain a fine powder which is fluid and not very pulverulent.

To obtain a granulated powder, a spray-drying tower of the M.S.D. type with the following parameters will be used:

tower inlet air temperature: 190° C.

tower outlet air temperature: 85° C.

plate/powder temperature: 69° C.

static bed temperature: 75° C.

This drying technique makes it possible to easily obtain uniform granules.

What is claimed is:

1. A method for producing a grape marc and/or seed tannin comprising:

(a) carrying out, starting with fresh black and/or white grape marc and/or seed, a solid-liquid extraction of a crude tannin fracfion in sulphited water ($H_2O+SO_2$);

(b) removing at least part of the aqueous solvent from the resulting extract in order to obtain a concentrate of the crude tannin fraction;

(c) obtaining a concentrate of the fermented crude tannin fraction by inoculating yeasts into the concentrate of the crude tannin fraction;

(d) purifying the crude tannin fraction in order to obtain the tannin by selective adsorption of the polyphenolic compounds of the concentrate onto a resin, elution of the polyphenolic compounds from the resin and subsequent filtration.

2. The method according to claim 1, wherein (a) is carried out at a temperature of 25° C. or less.

3. The method according to claim 2, wherein (a) is carried out at a temperature of between 15 and 25° C.

4. The method according to claim 1, wherein (b) is carried out by evaporation under vacuum at a temperature at most equal to 75° C.

5. The method according to claim 1, wherein, after evaporation, the concentrate of the crude tannin fraction is immediately cooled to a temperature at most equal to 30° C.

6. The method according to claim 1, wherein (c) is carried out by inoculating yeasts in suspension in a liquid medium into the concentrate of the crude tannin fraction; allowing to proceed yielding alcohol and suspended particles; and removing the formed alcohol and the particles in suspension.

7. The method according to claim 1, wherein in (d), the crude tannin fraction is absorbed on the resin, which is of the styrene DVB type.

8. The method according to claim 1, wherein the subsequent filtration is a diafiltration.

9. A method for producing a grape marc and/or seed tannin comprising:

(a) carrying out, starting with fresh black and/or white grape marc and/or seed, a solid-liquid extraction of a crude tannin fraction in water sulphited with 1 to 1.5 grams of sulfur dioxide per liter;

(b) removing at least part of the aqueous solvent from the resulting extract in order to obtain a concentrate of the crude tannin fraction;

(c) obtaining a concentrate of the fermented crude tannin fraction by inoculating yeasts into the concentrate of the crude tannin fraction;

(d) purifying the crude tannin fraction in order to obtain the tannin by selective adsorption of the polyphenolic compounds of the concentrate onto a resin, elution of the polyphenolic compounds from the resin and subsequent filtration.

* * * * *